US010210204B2

(12) United States Patent
Koziol

(10) Patent No.: US 10,210,204 B2
(45) Date of Patent: Feb. 19, 2019

(54) VOICE ACTUATED DATA RETRIEVAL AND AUTOMATED RETRIEVED DATA DISPLAY

(71) Applicant: Jeffrey E. Koziol, Arlington Heights, IL (US)

(72) Inventor: Jeffrey E. Koziol, Arlington Heights, IL (US)

( * ) Notice: Subject to any disclaimer, the term of this patent is extended or adjusted under 35 U.S.C. 154(b) by 0 days.

(21) Appl. No.: 14/741,315

(22) Filed: Jun. 16, 2015

(65) Prior Publication Data

US 2016/0098521 A1  Apr. 7, 2016

Related U.S. Application Data

(60) Provisional application No. 62/012,723, filed on Jun. 16, 2014.

(51) Int. Cl.
*G06F 19/00* (2018.01)
*G10L 15/26* (2006.01)
(Continued)

(52) U.S. Cl.
CPC .... *G06F 17/3043* (2013.01); *G06F 17/30401* (2013.01); *G06F 19/00* (2013.01);
(Continued)

(58) Field of Classification Search
CPC ............. G06F 19/322; G06F 17/30401; G06F 17/3043; G10L 15/22; G10L 2015/228
(Continued)

(56) References Cited

U.S. PATENT DOCUMENTS 6,728,676 B1 * 4/2004 Ortega ................. G06Q 20/203
704/231
6,766,297 B1 * 7/2004 Lamer ............... G06F 17/30011
704/270

(Continued)

FOREIGN PATENT DOCUMENTS

JP  08044796 A * 2/1996
WO  WO 2010110642 A2 * 9/2010 ............. G16H 40/63

OTHER PUBLICATIONS www.dummies.com, "How to Use Siri to Make Phone Calls", https://web.archive.org/web/20140219012236/http://www.dummies.com/how-to/content/how-to-use-siri-to-make-phone-calls.html, dated Feb. 19, 2014.*

(Continued)

*Primary Examiner* — Edwin S Leland, III
(74) *Attorney, Agent, or Firm* — Dickinson Wright, PLLC

(57) ABSTRACT

System platform, software and hardware equipment and components, and methodologies are provided for generating, organizing, storing and retrieving medical records using voice recognition in combination with unique codes assigned to data elements, and include microprocessor and memory, such as non-transient computer readable medium, having stored thereon a database including vocabulary terms. Speech recognition interface receives spoken language. Display generates an output according to vocabulary terms uniquely associated with the spoken language. Data stored in the database can include records organized into specific modules having specified vocabulary terms synced with each module and unique computer code to key vocabulary terms in the database. Using an associated unique code can cause specific data field to open on display when recognizing specific spoken word or phrase by the speech recognition interface.

7 Claims, 3 Drawing Sheets

(51) Int. Cl.
G06F 17/30 (2006.01)
G10L 15/08 (2006.01)
G10L 15/22 (2006.01)
G16H 10/60 (2018.01)

(52) U.S. Cl.
CPC .............. G10L 15/22 (2013.01); G16H 10/60 (2018.01); *G10L 2015/228* (2013.01)

(58) Field of Classification Search
USPC ..................................................... 704/270.1
See application file for complete search history.

(56) References Cited

U.S. PATENT DOCUMENTS

| | | | | |
|---|---|---|---|---|
| 8,489,398 | B1* | 7/2013 | Gruenstein | G10L 15/08 704/231 |
| 8,832,546 | B2* | 9/2014 | Begole | G06F 17/243 715/226 |
| 8,850,304 | B2* | 9/2014 | Ye | G06Q 30/08 715/226 |
| 9,043,299 | B2* | 5/2015 | Vendelin | G06F 17/3028 707/706 |
| 9,237,842 | B2* | 1/2016 | Lee | A61B 3/0041 |
| 2002/0143533 | A1* | 10/2002 | Lucas | G06F 3/167 704/235 |
| 2002/0194029 | A1* | 12/2002 | Guan | G06Q 10/10 705/3 |
| 2005/0055215 | A1* | 3/2005 | Klotz | G10L 15/26 704/275 |
| 2007/0124149 | A1* | 5/2007 | Shen | G10L 15/26 704/275 |
| 2009/0132286 | A1* | 5/2009 | Blaquier | G06Q 50/22 705/3 |
| 2009/0177477 | A1* | 7/2009 | Nenov | A61B 5/0002 704/275 |
| 2010/0324899 | A1* | 12/2010 | Yamabana | G10L 15/07 704/251 |
| 2011/0075901 | A1* | 3/2011 | Nakamura | G06F 19/321 382/128 |
| 2013/0308839 | A1* | 11/2013 | Taylor | G06F 19/321 382/128 |
| 2014/0163994 | A1* | 6/2014 | Lau | H04M 1/271 704/275 |
| 2014/0350928 | A1* | 11/2014 | Zeigler | G10L 15/26 704/235 |
| 2015/0019226 | A1* | 1/2015 | Gazdzinski | G06Q 30/0251 704/254 |
| 2016/0098521 | A1* | 4/2016 | Koziol | G06F 19/322 704/270.1 |

OTHER PUBLICATIONS teachmeios.com, "How to create iCloud contact groups for iPhone, iPad (Mini, Air) and iPod Touch", http://teachmeios.com/how-to-create-icloud-contact-groups-for-iphone-ipad-mini-air-and-ipod-touch/, dated Mar. 9, 2014.* imore.com, "Contact Pictures on iPhone 5S", http://forums.imore.com/iphone-5s/264494-contact-pictures-iphone-5s.html, dated Sep. 28, 2013.* www.apple.com, "Apple iPhone 4S Technical Specifications", https://www.apple.com/lae/iphone-4s/specs/, retreived Jun. 25, 2016.*

* cited by examiner

VOICE ACTUATED DATA RETRIEVAL AND AUTOMATED RETRIEVED DATA DISPLAY

CROSS-REFERENCE TO RELATED APPLICATIONS

This application claims priority to prior U.S. Provisional Patent Application No. 62/012,723, filed Jun. 16, 2014, the entire content of which is incorporated herein by reference.

BACKGROUND OF THE INVENTION

1. Field of the Invention

Generally, exemplary embodiments of the present invention relate to the fields of generating, organizing and storing of records. Exemplary implementations of certain embodiments of the invention provide systems and methods for generating, organizing, storing and retrieving medical records using voice recognition in combination with unique codes assigned to data elements.

2. Discussion of the Background of the Invention

Presently, physicians have to meet electronic medical record (EMR) guidelines to be compliant with government regulations. Medical records are voluminous with as many as 20 pages or more of records associated with each patient's medical visit. In order to comply with the EMR guidelines, doctors find that more time is spent manually entering data on the computer during patient examination than attending to the patient. Conventionally, there are voice recognition protocols and methods that my facilitate data entry without having to do so manually. When using such conventional methods or systems, a doctor may audibly dictate notes during a patient's visit and have those notes converted to text, or can provide verbal commands to a computing device with voice recognition software and hardware to, for example, display or edit stored information.

However, such conventional systems and methods are not well equipped to address the specific needs of medical data entry, particularly in a way that would facilitate meaningful organization, storage, and retrieval of medical data which uses unique terminology and requires specific format, forms, and the manner in which data is output and displayed. For example, simply converting dictation to a text file would not meet EMR guidelines, as information cannot be in a text file but needs to be in a database in a certain form.

SUMMARY OF THE INVENTION

Exemplary embodiments of the present invention address at least these issues by providing systems and methods using speech recognition for a doctor's medical records where a medical record is organized into specific modules having specified vocabulary synced with each module and a unique computer code to key vocabulary words in a database.

An exemplary embodiment of the present invention provides a system for generating and organizing medical records including a microprocessor and a memory, such as a non-transient computer readable medium, having stored thereon a database including vocabulary terms, a speech recognition interface receiving spoken language, and a display generating an output according to vocabulary terms uniquely associated with the spoken language. In an exemplary implementation of embodiments of the present invention, data stored in the database includes records organized into specific modules having specified vocabulary terms synced with each module and a unique computer code to key vocabulary terms in the database.

In a further exemplary implementation of embodiments of the present invention, the use of an associated unique code causes a specific data field to open on the display when recognizing a specific spoken word or phrase by the speech recognition interface.

Another exemplary embodiment of the present invention provides a system for compiling, organizing and presenting information contained in medical records including a second display in communication with the microprocessor such that the output of the second display is interactively associated with recognized vocabulary terms and comprises relevant information in an illustrative and explanatory format including visual, textual, and/or audio information to facilitate understanding.

Yet another exemplary embodiment of the present invention provides a method for generating and organizing medical records including storing in a memory, such as non-transient computer readable medium, a database including vocabulary terms and associating a unique code with at least a selected plurality of the vocabulary terms in the database. The method further providing for a computer generated graphical interface selectively performing a predetermined function in accordance with a unique code associated with at least one of the selected plurality of vocabulary terms.

BRIEF DESCRIPTION OF THE DRAWINGS

A more complete appreciation of the present invention and many of the attendant advantages thereof will be readily obtained as the same becomes better understood by reference to the following detailed description when considered in connection with the accompanying drawings, wherein FIG. 1 provides an illustrative example of topology and architecture, as well as certain exemplary display characteristics, of a system and methodology according to exemplary embodiments of the present invention.

DETAILED DESCRIPTION OF EXEMPLARY EMBODIMENTS

The matters exemplified in this description are provided to assist in a comprehensive understanding of exemplary embodiments of the invention. Accordingly, those of ordinary skill in the art will recognize that various changes and modifications of the embodiments described herein can be made without departing from the scope and spirit of the described invention. Also, descriptions of well-known functions and constructions are omitted for clarity and conciseness.

In an exemplary implementation of the present invention, each module comprises an associated small unique vocabulary, and the use of an associated unique code causes a specific data field to open when recognizing a specific spoken word or phrase.

According to exemplary embodiments of the present invention, a voice activated medical record fills in an associated data field as the doctor talks to the patient based on recognition of a specific spoken word or phrase. The available vocabulary would be restricted to the highlighted fields. This could be what is on the computer screen at the time or organized by exam elements.

In an exemplary implementation of the present invention, available vocabulary can include terms that are specific to a certain field of practice. For example and without limitation, for ophthalmology, vocabulary terms can include elements of the anterior segment, posterior segment, refraction and so on. All physicians' records have elements of past medical history, chief complaint, allergies, medication, past surgeries and so on. According to exemplary embodiments of the present invention, a system would fill in data fields in front of the doctor and patient and would not be a dictation system to put in text. One of the advantages of such a system is achieved by restricting vocabulary choices to that which is used in that element making voice recognition during patient examination easier and more accurate.

Figure 1:
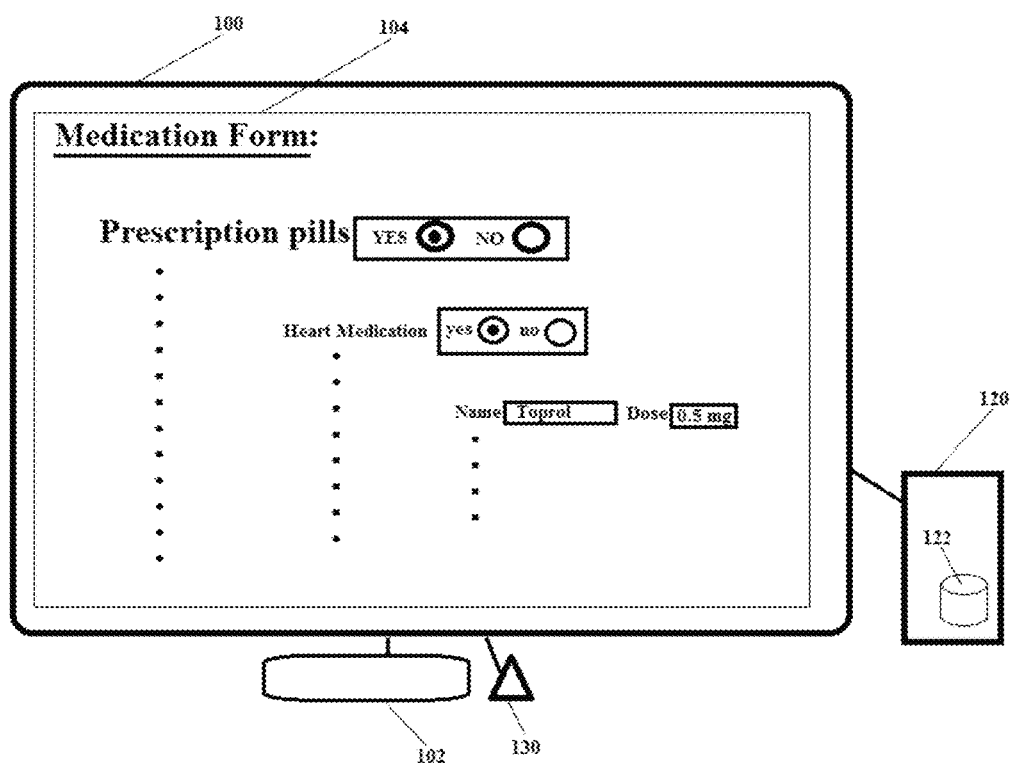

Referring to an example of FIG. 1, a doctor may inquire about a patient's medication, in which case when audio input 130 detects a particular term from the spoken inquiry, a "medication form" screen 104 can be displayed on doctor's computer 100, and when the system, including computer 120, recognizes associated vocabulary terms, such as "prescription pills" for example, stored on non-transient computer readable medium 122, it fills in the yes/no field accordingly on medical form screen 104 without doctor interaction with a manual input device 102 such as a keyboard. Further spoken inquiry may include recognized vocabulary terms such as "heart medication" filling in the yes/no field accordingly. Still further inquiry may include recognized vocabulary terms such as "name" of the medication and "dosage" filling in the associated fields with terms such as name "Toprol" and dosage "0.5 mg" as recognized by the system.

Figure 2:
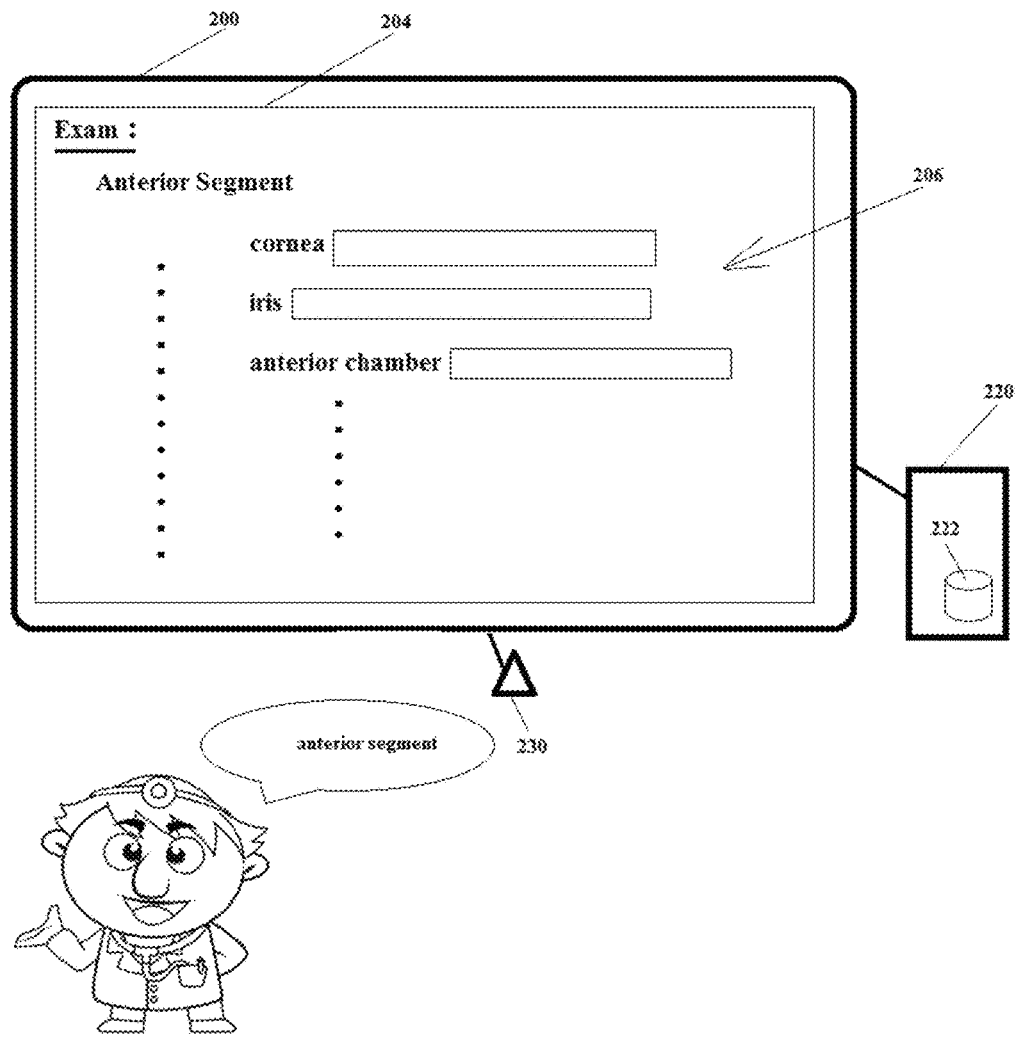
FIG. 2 is a generalized illustration of certain functionality provided by a system and methodology according to an exemplary embodiment of the present invention in the field of ophthalmology.

According to an exemplary embodiment of the present invention, a unique computer code (or an identifier) can be attached to key vocabulary words in a database. The code is associated with a specific data field which is opened when the word is spoken. A non-limiting example of such an implementation in ophthalmology can be applied to an exam called an anterior segment as conceptually illustrated in FIG. 2, where in a vocabulary database 222 "anterior segment" is stored as "anterior segment: -code-code-code". The code can be any, for example, alphanumeric, representation, such as a six digit number. This data field has a number of specific subfields describing the cornea, iris, anterior chamber and so on. When a doctor speaks "anterior segment" into an audio pick up 230, this data field would open screen 204 of doctor computer 200 and a group of key words with code attached would direct entries into specific data fields 206. When it is time for the next data field, the doctor would speak the name of the next field and the present field would close and the next field would open.

In yet another exemplary implementation of the present invention, a patient education screen can be interactively associated with recognized vocabulary terms providing relevant information to the patient in an easily understandable format including explanatory visual or verbal information to help facilitate patient understanding. For example, if the patient has cataracts, a display can be initialized to visually demonstrate an eye with a cataract and, for example, audibly or textually provide any additional explanatory information or treatment options.

Figure 3:
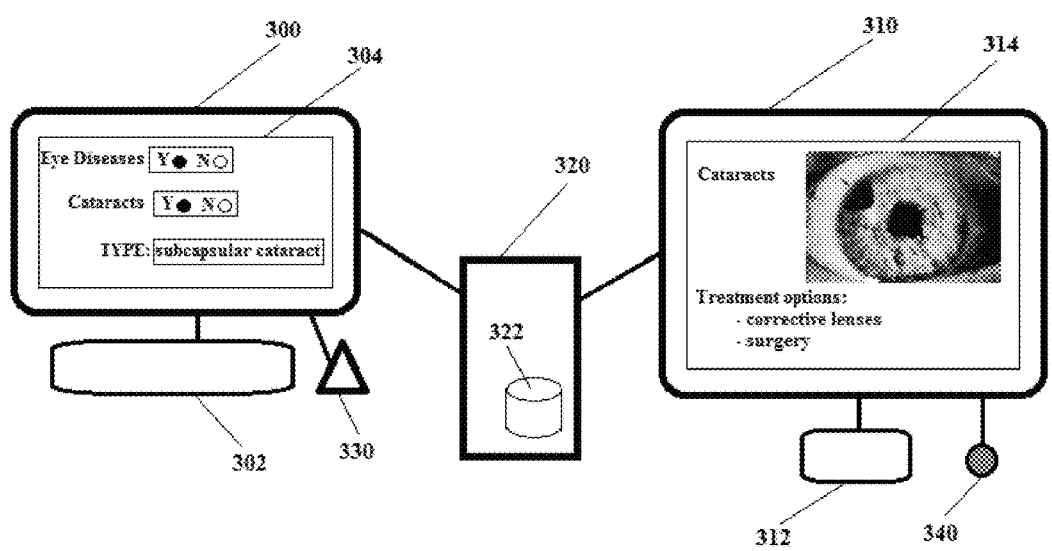
FIG. 3 provides an illustrative example of topology and architecture, as well as certain complementary component features, of a system and methodology according to yet further exemplary embodiments of the present invention.

Referring to a conceptual diagram of FIG. 3, according to yet another exemplary embodiment of the present invention, associated explanatory information can be provided to a patient in real time by, for example, having two monitors: one designated as a patient education screen or monitor or computer generated graphical interface 310 and the other as a doctor medical record screen or monitor or computer generated graphical interface 300. In an exemplary implementation, a system and method can include a computer 320, having a non-transient computer readable medium 322 having stored thereon a database comprising vocabulary terms organized and accessible in accordance with exemplary embodiments of the present invention, as well as explanatory information associated with selected terms, a doctor monitor 300 (together with an input interface 302, such as a keyboard, and voice recognition interface 330 including, for example, a microphone), and a patient monitor 310.

According to exemplary embodiments of the present invention, the medical record monitor 300 would display 304 to the doctor specific fields in a selected electronic medical form being filled in as the system recognizes the vocabulary terms in the doctor's speech, while the patient education monitor 310 would display 314 to the patient explanatory information associated with the recognized vocabulary terms (audio explanation can be provided via an audio output device 340, such as a speaker associated with the education screen 310). The respective information associated with the recognized vocabulary terms can be displayed to the doctor and the patient essentially simultaneously.

In yet another exemplary implementation, information displayed to the patient can be selectively initiated and controlled by the doctor via interface 302 or 330. In yet further exemplary implementation, limited or unlimited selective control of display of the information available for patient education monitor 310 via interface 312 can be granted to the patient. For example, interface 312 can comprise anything from a full function keyboard to a single volume control knob, depending on the desired level of control of patient education monitor 310 to be made selectively available to a patient.

The above-described exemplary embodiments may be recorded in computer-readable media including program instructions to implement various operations embodied by a computer. The media may also include, alone or in combination with the program instructions, data files, data structures, and the like. The media and program instructions may be those specially designed and constructed for the purposes of the present invention, or they may be of the kind well-known and available to those having skill in the computer software arts. Examples of computer-readable media include magnetic media such as hard disks, floppy disks, and magnetic tape; optical media such as CD-ROM disks and DVD; magneto-optical media such as optical disks; and hardware devices that are specially configured to store and perform program instructions, such as read-only memory (ROM), random access memory (RAM), flash memory, and the like. The media may also be a transmission medium such as optical or metallic lines, wave guides, and so on, including a carrier wave transmitting signals specifying the program instructions, data structures, and so on. Examples of program instructions include both machine code, such as produced by a compiler, and files containing higher level code that may be executed by the computer using an interpreter. The described hardware devices may be configured to act as one or more software modules in order to perform the operations of the above-described embodiments of the present invention.

Other objects, advantages and salient features of the invention will become apparent to those skilled in the art from the details provided, which, taken in conjunction with the accompanying drawing figures, disclose exemplary embodiments of the invention.

While the present invention has been shown and described with reference to certain exemplary embodiments thereof, it will be understood by those skilled in the art that various changes in form and details may be made therein without departing from the spirit and scope of the present invention.

I claim:

1. A system for automatically retrieving and filling in data fields in electronic medical forms, comprising:
   a microprocessor in communication with a non-transient computer readable medium having stored thereon a database comprising a plurality of vocabulary terms, unique identifiers assigned to said vocabulary terms, and a plurality of medical records organized into modules each synchronized with at least one of said unique identifiers;
   an audio input detecting a spoken language;
   a display in communication with said microprocessor outputting information associated with at least a portion of said plurality of medical records; and
   a speech recognition interface adapted to communicate with said microprocessor and said audio input and configured to output based on said communication a digital representation of at least one of said vocabulary terms to said microprocessor when said spoken language includes an audio representation of said at least one of said vocabulary terms and only if said at least one of said vocabulary terms is associated with said portion of said plurality of medical records output on said display,
   said microprocessor including a non-transient memory storing computer readable instructions and one or more processors couple to said memory, and when executing said computer readable instructions configured to control said display based on said output from said speech recognition interface to
      generate an output on said display according to at least one of said unique identifiers assigned to said at least one of said vocabulary terms having said digital representation,
      open at least one data field within said display uniquely associated with at least one of said unique identifiers assigned to said at least one of said vocabulary terms having said digital representation, and
      direct at least a portion of said plurality of medical records from at least one of said modules synchronized with said at least one of said unique identifiers assigned to said at least one of said vocabulary terms having said digital representation into said at least one opened data field.

2. The system as claimed in claim 1, wherein, when said display displays said portion of said plurality of medical records from said at least one of said modules in said at least one open data field,
   said speech recognition interface receives another spoken language and outputs another digital representation of at least one another of said vocabulary terms to said microprocessor when said received another spoken language includes another audio representation of said at least one another of said vocabulary terms recognized by said speech recognition interface and only if said at least one another of said vocabulary terms is associated with said portion of said plurality of medical records output on said display; and
   said microprocessor when executing said computer readable instructions is configured to control said display to
      open at least one another data field on said display uniquely associated with at least one of another of said unique identifiers assigned to said at least one another of said vocabulary terms having said another digital representation, and
      direct at least another portion of said plurality of medical records from at least one of said modules synchronized with said at least one another of said unique identifiers assigned to said at least one another of said vocabulary terms having said another digital representation into said at least one another opened data field.

3. The system as claimed in claim 2, wherein said microprocessor when executing said computer readable instructions is configured to control said display to close said at least one previously opened data field when said speech recognition interface outputs another digital representation of at least one other of said vocabulary terms.

4. The system as claimed in claim 1, wherein said medical records comprise elements of a patient's medical history associated with at least one of said plurality of vocabulary terms.

5. The system as claimed in claim 4, wherein said display outputs at least one of said elements associated with at least one of said plurality of vocabulary terms recognized by said speech recognition interface.

6. The system as claimed in claim 1, further comprising a second display in communication with said microprocessor, wherein an output of said second display is interactively associated with said recognized audio representation of said at least one of said vocabulary terms, and comprises at least one of visual, textual, and audio information associated with said at least one of said vocabulary terms.

7. The system as claimed in claim 6, wherein said output on said second display comprises information in an illustrative and explanatory format relevant to said at least one of said vocabulary terms.

* * * * *